United States Patent [19]

Henrick et al.

[11] 4,006,188
[45] Feb. 1, 1977

[54] CYCLOALKENONES

[75] Inventors: Clive A. Henrick; Jeffery N. Labovitz, both of Palo Alto, Calif.

[73] Assignee: Zoecon Corporation, Palo Alto, Calif.

[22] Filed: Apr. 30, 1976

[21] Appl. No.: 681,968

Related U.S. Application Data

[60] Division of Ser. No. 590,231, June 25, 1975, which is a continuation-in-part of Ser. No. 464,880, April 29, 1974, abandoned.

[52] U.S. Cl. .................. 260/586 R; 260/455 R; 260/468 H; 260/514 H; 260/557 R; 260/544 L; 424/299; 424/301; 424/320

[51] Int. Cl.² ............... C07C 49/46; C07C 49/45; C07C 49/48

[58] Field of Search ............... 260/586 R

[56] References Cited

UNITED STATES PATENTS

| | | | |
|---|---|---|---|
| 3,478,104 | 11/1969 | Surmatis | 260/586 R |
| 3,576,880 | 4/1971 | Weedon et al. | 260/586 R |
| 3,886,185 | 5/1975 | Alvarez et al. | 260/586 R |
| 3,925,477 | 12/1975 | Frater et al. | 260/586 R |

Primary Examiner—Lewis Gotts
Assistant Examiner—D. R. Phillips
Attorney, Agent, or Firm—Donald W. Erickson

[57] ABSTRACT

Novel aliphatic di- and tri-olefinic acids, esters, thio S-acids, S-thioates, ketones and amides, intermediates therefor, and the control of insects therewith.

8 Claims, No Drawings

CYCLOALKENONES

This is a division of application Ser. No. 590,231, filed June 25, 1975, which in turn is a continuation-in-part of application Ser. No. 464,880, filed Apr. 29, 1974, now abandoned.

This invention relates to novel aliphatic di- and tri-olefinic compounds, intermediates therefor and the control of insects therewith.

The novel compounds of this invention that are useful for the control of insects or as intermediates therefor are represented by the following formula I:

$$R^4-\underset{\underset{Z}{|}}{\overset{\overset{R^3}{|}}{C}}-\underset{\underset{Z'}{|}}{\overset{\overset{R^5}{|}}{C}}-(CH_2)_n-\overset{\overset{R^2}{|}}{CH}-CH_2-\underset{\underset{\underset{H}{|}}{C}}{\overset{R^6}{\overset{/\quad\backslash}{C}}}\overset{R^1}{\underset{\|}{C}}=\overset{}{C}-Q \qquad (I)$$

wherein,
R$^1$ is hydrogen or lower alkyl;
R$^2$ is lower alkyl;
R$^3$ is hydrogen or lower alkyl;
R$^4$ is lower alkyl;
R$^5$ is hydrogen or lower alkyl;
Z is hydrogen, chlorine, lower alkyl or one of the groups —OR or —SR in which R is hydrogen or lower alkyl;
Z' is hydrogen or together with Z forms a carbon-carbon bond;
n is one, two or three;
R$^6$ is methylene, ethylene or trimethylene;
Q is one of the groups $$-\overset{\overset{O}{\|}}{C}-OR^7,\quad -\overset{\overset{O}{\|}}{C}-SR^7,\quad -\overset{\overset{O}{\|}}{C}-N\overset{R^8}{\underset{R^9}{\diagdown}},\quad\text{or}\quad -\overset{\overset{O}{\|}}{C}-R^{10}$$

in which,
R$^7$ is lower alkyl, lower alkenyl, lower alkynyl, cycloalkyl or cycloalkalkyl;
each of R$^8$ and R$^9$ is hydrogen, lower alkyl, lower alkenyl, cycloalkyl or cycloalkalkyl; and
R$^{10}$ is lower alkyl.

The compounds of formula I are useful for the control of insects. The utility of these compounds as insect control agents is believed to be attributable to their juvenile hormone activity. They are preferably applied to the immature insect, namely - during the embryo, larvae or pupae stage in view of their effect on metamorphosis and causing abnormal development leading to death or inability to reproduce. These compounds are effective control agents for Hemipteran such as Lygaeidae, Miridae and Pyrrhocoridae; Lepidopteran such as Pyralidae, Noctuidae and Gelechiidai; Coleopteran such as Tenebrionidae, Crysomelidae and Dermestidae; Dipteran such as mosquitos, flies, Homopteran such as aphids and other insects. The compounds can be applied at low dosage levels of the order of 0.001 μg. to 25.0 μg. per insect. Suitable carrier substances include liquid or solid carriers, such as water, acetone, xylene, mineral or vegetable oils, talc, vermiculite, natural and synthetic resins and silica. Treatment of insects in accordance with the present invention is accomplished by spraying, dusting or exposing the insects to the vapor of the compounds of formula I. Generally, a concentration of less than 25% of the active compound is employed. The formulations can include insect attractants, emulsifying agents or wetting agents to assist in the application and effectiveness of the active ingredient. In the application of the compounds, there is generally employed a mixture of the C-2,3 trans and cis isomers.

In the description hereinafter, each of R, R$^1$–R$^{10}$, Q Z, Z', and n is as defined above unless otherwise specified.

In one embodiment of the present invention, there is provided carboxylic esters included within formula I above of the following formula A:

$$R^4-\underset{\underset{Z''}{|}}{\overset{\overset{R^3}{|}}{C}}-\underset{\underset{Z'}{|}}{\overset{\overset{R^5}{|}}{C}}-(CH_2)_n-\overset{\overset{R^2}{|}}{CH}-CH_2-\underset{}{\overset{R^6}{\overset{/\quad\backslash}{C}}=CH}-\overset{\overset{R^1}{|}}{C}=\overset{\overset{O}{\|}}{C}-OR^7 \qquad (A)$$

wherein R, R$^{1-6}$, and n are as defined above; R$^7$ is lower alkyl; Z" is hydrogen, lower alkyl, or —SR, and Z' is hydrogen or together with Z" forms a carbon-carbon bond.

One synthesis of the carboxylic esters of formula A can be outlined as follows:

$$R^4-\underset{\underset{Z''}{|}}{\overset{\overset{R^3}{|}}{C}}-\underset{\underset{Z'}{|}}{\overset{\overset{R^5}{|}}{C}}-(CH_2)_n-\overset{\overset{R^2}{|}}{CH}-CH_2MgBr \qquad (B)$$

$$\downarrow \quad H_3C-O-\overset{R^6}{\overset{/\quad\backslash}{C}}=CH-C=O \qquad (C)$$

$$R^4-\underset{\underset{Z''}{|}}{\overset{\overset{R^3}{|}}{C}}-\underset{\underset{Z'}{|}}{\overset{\overset{R^5}{|}}{C}}-(CH_2)_n-\overset{\overset{R^2}{|}}{CH}-CH_2-\overset{R^6}{\overset{/\quad\backslash}{C}}=CH-C=O \qquad (II)$$

$$\downarrow \quad R^7O\overset{\overset{O}{\|}}{C}-CH_2Li \quad\text{or}\quad LiO\overset{\overset{O}{\|}}{C}-CH_2Li$$

$$\downarrow$$

-continued

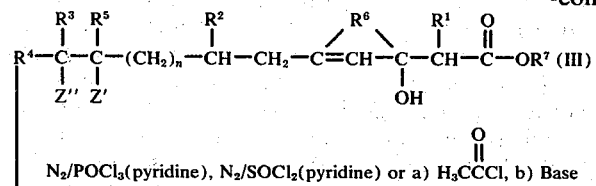

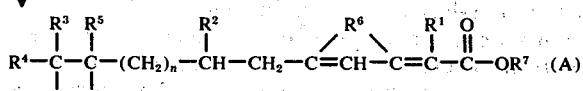

In the above synthesis, a Grignard compound of Formula B, wherein Z'' Z' is as defined above, is reacted, under a nitrogen atmosphere, with a 3-methoxy-cycloalk-2-en-1-one of Formula C to yield a 3-substituted cycloalk-2-en-1-one of Formula II, which is then treated with the appropriate organo-lithium compound at —80° C under nitrogen to yield the 3-hydroxy compound of Formula III (or the acid thereof) which is then dehydrated to the corresponding ester of Formula A (or the acid thereof).

The Grignard reagent is prepared by contacting the corresponding 1-bromo compound (b'):

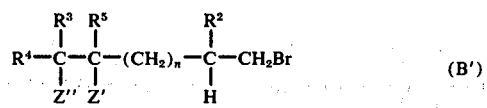

with magnesium metal in ether solution under nitrogen. Those 1-bromo compounds wherein Z'' is hydrogen, lower alkyl, or —SR can be conveniently prepared, for example, by treating the corresponding 1-ene compound with boron hydride in tetrahydrofuran followed by bromine with strong base such as sodium methoxide. Those 1-bromo compounds wherein Z and Z' form a carbon-carbon bond are conveniently prepared by treating an aldehyde of the formula (E)

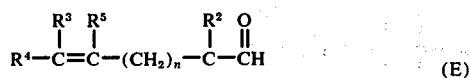

with sodium borohydride to obtain the corresponding alcohol and then treating with, for example, phosphorus tribromide to yield the desired 1-bromo compound or via the tosylate.

The aldehydes of Formula E can be prepared using the procedures of Henrick and Siddall, U.S. Pat. No. 3,755,411.

Compounds of Formula C are conveniently prepared by treating the corresponding 1,3-cycloalkanedione with diazomethane in the presence of methanol and ether to yield the desired 3-methoxy-cycloalk-2-en-1-one.

A second synthesis of the carboxylic esters of formula I can be outlined as follows:

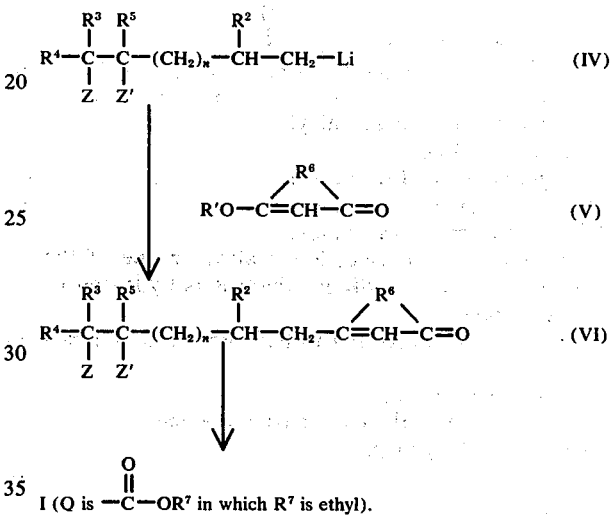

I (Q is $-C-OR^7$ in which $R^7$ is ethyl).

In the practice of the above outlined synthesis, a lithium reagent (IV) is reacted with a lower alkoxy-cycloalk-2-en-1-one (R' is lower alkyl) of formula V to prepare an enone of formula VI. The reaction is carried out at room temperature or lower in an ether solvent. The enone VI is then reacted with ethyl lithiotrimethyl-silylacetate at room temperature or lower to yield the ethyl ester of Formula I (Q is —CO$_2$Et). Cf. Taguchi et al, Bull. Chem. Soc. Japan 47 (10), 2529 (1974).

The carboxylic esters can be converted into the corresponding acid by hydrolysis with base such as potassium hydroxide, sodium carbonate, sodium hydroxide, and the like in organic solvent such as methanol or ethanol. Other esters of Formula I can be prepared by transesterification or conversion of the acid into the acid halide by treatment with thionyl chloride, oxalyl chloride, phosphorus pentabromide or the like, and then reacting the acid halide with the alcohol corresponding to the ester moiety desired.

In a second embodiment of the novel compounds of the present invention, there is provided S-thioates of Formula I and thio-S-acids. S-Thioates

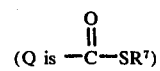

can be prepared from the respective acid halide using hydrogen sulfide to prepare the thio-S-acid and a thiol R$^7$—SH in pyridine or a mercaptide to prepare the S-thioates. S-thioates can be prepared by alkylation of the sodium salt of a thio S-acid of the present invention also. See U.S. Pats. Nos. 3,567,747 and 3,503,366.

In another embodiment of the present invention, there is provided ketones of Formula I wherein Q is the group

These ketones can be prepared by treatment of an ester of Formula I or acid thereof with the appropriate organolithium of the formula Li—$R^{10}$. The reaction is generally carried out in an organic solvent such as an ether solvent. In addition, the ketones can be prepared by forming the acid halide, particularly the acid chloride, corresponding to Formula I and reacting with lithium diorganocopper, e.g. lithium dimethylcopper, using the procedure of Posner and Whitten, Tetrahedron Letters, No. 53, 4647 (1970).

Compounds of Formula I wherein Q is the group

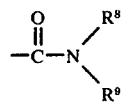

can be prepared by treating a carboxylic acid halide with an amine of the formula

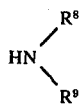

The compounds of Formula I wherein Z' is hydrogen and Z is chloro can be prepared by treating a compound of Formula I wherein Z and Z' form a carbon-carbon bond with hydrogen chloride in carbon tetrachloride or other halogenated hydrocarbon solvent of low dielectric constant.

The compounds of Formula I wherein Z' is hydrogen, Z is —OR can be prepared by the reaction of a compound of Formula I wherein Z and Z' form a carbon-carbon bond with an alcohol of the formula ROH in the presence of a mercuric salt followed by reduction of the oxy-mercurial intermediate in situ. Conducting the reaction in the presence of water provides the compounds wherein Z is hydroxy. Suitable mercuric salts include mercuric acetate, mercuric nitrate, mercuric trifluoroacetate, mercuric acylates and mercuric halides. Suitable reducing agents include the borohydrides, hydrazine and sodium amalgam. See Brown and Rei, *J. Am. Chem. Soc.* 91, 5646 (1969); Brown et al., *J. Am. Chem. Soc.* 89, 1522 and 1524 (1957); and Wakabayashi, *J. Med. Chem.* 12, 191 (January 1969).

The corresponding S-thioates, thio S-acids, amides and ketones can be prepared using the appropriate procedures as described above.

The term "lower alkyl", as used herein, refers to a saturated aliphatic hydrocarbon, branched or straight chain, of one to six carbon atoms. The term "lower alkenyl" refers to an ethylenically unsaturated hydrocarbon group, straight or branched chain, of three to six carbon atoms. The term "lower alkynyl" refers to an acetylenically unsaturated hydrocarbon group, straight or branched chain, of three to six carbon atoms.

The term "cycloalkyl", as used herein, refers to a cycloalkyl group of three to eight carbon atoms. The term "cycloalkalkyl", as used herein, refers to a cycloalkalkyl group of four to nine carbon atoms such as cyclopropanemethyl, cyclopropaneethyl, cyclopropanemethyl, and the like.

As used herein, the terms "methylene", "ethylene", and "trimethylene" refer to the groups —$CH_2$, —$CH_2$—$CH_2$—, and —$CH_2$—$CH_2$—$CH_2$— respectively.

The olefinic bond present in the cycloalkene ring portion of the compounds of Formula I has a configuration as shown in the drawing of Formula I. In the application of the compounds of the present invention for the control of insects, the isomerism is preferably trans or mostly trans at

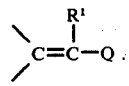

The following examples are provided to illustrate the practice of the present invention. Temperature is given in degrees Centigrade, boiling points are for short path distillation.

EXAMPLE I

To a solution of 10.75 g. of 2,6-dimethyl-1-heptene in 45 ml. tetrahydrofuran is added 30 ml. of a 1 M solution of diborane in tetrahydrofuran while the temperature of the reaction mixture is maintained at —10° to —20°. The reaction mixture is stirred at 0° for 45 minutes and then at 20° for 30 minutes. Methanol (1 ml.) is added to destroy any excess diborane. While maintaining the temperature of the reaction mixture below 25°, 13.55 g. bromine and 5.05 g. sodium methoxide are slowly added. The reaction mixture is stirred for one-half hour at 25°, followed by the addition of 25 ml. pertane, 20 ml. water and 20 ml. saturated aqueous potassium carbonte. The pentane layer is separated, washed, in turn, with water and saturated brine, dried over sodium sulfate and the product distilled to yield 9.03 g. of 1-bromo-2,6-dimethylheptane, b.p. 62°-64° at 2.5 mm.

Following the procedure of Example I using the olefins of Column I, the bromides of Column II are prepared.

I 2,5-diethyl-1-hexene
2,4,5-trimethyl-1-hexene
2,5,5-trimethyl-1-hexene
2,5-dimethyl-1-heptene
2,4,5-trimethyl-1-heptene
2,5,5-trimethyl-1-heptene
2-methyl-1-hexene
2,5,5-triethyl-1-hepeten
2,6-dimethyl-1-octene
2,5,6-trimethyl-1-heptene
2,5,6-trimethyl-1-octene
2-methyl-1-heptene
2-methyl-1-octene
2,6-diethyl-1-heptene
2,6-diethyl-1-octene
6-methyl-2-ethyl-1-heptene 6-methyl-2-ethyl-1-octene
2,6,6-trimethyl-1-heptene
2,6,6-trimethyl-1-octene

II 1-bromo-2,5-diethylhexane
1-bromo-2,4,5-trimethylhexane
1-bromo-2,5,5-trimethylhexane
1-bromo-2,5-dimethylheptane
1-bromo-2,4,5-trimethylheptane
1-bromo-2,5,5-trimethylheptane
1-bromo-2-methylhexane
1-bromo-2,5,5-triethylheptane
1-bromo-2,6-dimethyloctane
1-bromo-2,5,6-trimethylheptane
1-bromo-2,5,6-trimethyloctane
1-bromo-2-methylheptane
1-bromo-2-methyloctane
1-bromo-2,6-diethylheptane
1-bromo-2,6-diethyloctane
1-bromo-2-ethyl6-methylheptane
1-bromo-2-ethyl-6-methyloctane
1-bromo-2,6,6-trimethylheptane
1-bromo-2,6,6-trimethyloctane Those 1-bromo compounds (B') wherein unsaturation at the 4 or 5 position or Z" is the group —SR is desired are prepared by treating the corresponding 1-aldehyde with sodium borohydride in methanol to yield the 1-alcohol and brominating with phosphorus tribromide or phosphorus pentabromide. Using this process, the bromides of Column III can be prepared.

III 1-bromo-2,6-dimethyl-6-methylthioheptane
1-bromo-2,6-dimethyl-5-heptene
1-bromo-5-ethylthio-2,4,5-trimethylhexane
1-bromo-2,5-dimethyl-5-hexene
1-bromo-5-ethyl-2-methyl-5-methylthioheptane
1-bromo-2,5-dimethyl-4-heptene
1-bromo-2-ethyl-5-methyl-5-methylthioheptane
1-bromo-2-ethyl-6-methyl-5-heptene
1-bromo-2,4,5-triethyl-4-hexene
1-bromo-2,5-diethyl-5-methylthiohexane
1-bromo-2-ethyl-3-methyl-5-octene
1-bromo-2-ethyl-6-methyl-6-methylthioheptane
1-bromo-2,5,6-trimethyl-5-heptene
1-bromo-6-ethylthio-2,5,6-triethylheptane
1-bromo-2,6-diethyl-5-octene

EXAMPLE 2

To a solution of 100 g. potassium hydroxide, 300 ml. water and 600 ml. ether at 0° is added 15 g. of N-methyl-N'-nitrosoguanidine. The ether layer is decanted off and is dried over solid potassium hydroxide. The ether layer (containing diazomethane) is then added, at 0°, to 3.00 g. of 1,3-cyclopentanedione. After stirring for 45 minutes, the excess solvent and diazomethane is removed by evaporation to yield 3.16 g. of 3-methoxycyclopent-2-en-1-one, b.p. 91° at 2.5 mm.

Using the procedure of Example 2 with stirring of the reaction mixture for up to one day, 3-methoxycyclobut-2-en-1-one and 3-methoxycyclohex-2-en-1-one are prepared from 1,3-cyclobutanedione and 1,3-cyclohexanedione.

EXAMPLE 3

To 1.70 g. magnesium metal in 10 ml. ether, under nitrogen, is slowly added, over 1 hour, 9.30 g. of 1-bromo-2,6-dimethylheptane in 20 ml. ether. The mixture is refluxed for three hours.

Using this procedure, the corresponding Grignard reagents are prepared for each of the bromides of Columns II and III.

EXAMPLE 4

To the Grignard reagent prepared in Example 3 is added, at 0°, over a period of 1 ½ hours, 3.16 g. of 3-methoxycyclopent-2-en-1-one in 30 ml. ether. The solution is stirred at room temperature for one day. 150 ml. of 1N sulfuric acid is added at 0° over a period of 1 ½ hours. The reaction mixture is stirred for four hours. The product is then extracted, dried over sodium sulfate and purified by distillation and preparative thin layer chromatography (9:1 hexane-ethyl acetate) to yield 1.00 g. of 3-(2,6-dimethylheptyl)-cyclopent-2-en-1-one, b.p. 72° at 0.03 mm.

Following the procedure of Example 4, the ketones of Column IV are prepared from the Grignard reagents prepared according to Example 3 and the ketones of Example 2.

IV 3-(2,5-diethylhexyl)-cyclopent-2-en-1-one
3-(2,4,5-trimethylhexyl)-cyclopent-2-en-1-one
3-(2,5,5-trimethylhexyl)-cyclopent-2-en-1-one
3-(2,5-dimethylheptyl)-cyclopent-2-en-1-one
3-(2,4,5-trimethylheptyl)-cyclopent-2-en-1-one
3-(2,5,5-trimethylheptyl)-cyclopent-2-en-1-one
3-(2-methylhexyl)-cyclopent-2-en-1-one
3-(2,5,5-trimethylheptyl)-cyclopent-2-en-1-one
3-(2,6-dimethyloctyl)-cyclopent-2-en-1-one
3-(2,5,6-trimethylheptyl)-cyclohex-2-en-1-one
3-(2,5,6-trimethyloctyl)-cyclohex-2-en-1-one
3-(2-methylheptyl)-cyclohex-2-en-1-one
3-(2-methyloctyl)-cyclohex-2-en-1-one
3-(2,6-diethylheptyl)-cyclohex-2-en-1-one
3-(2-methyloctyl)-cyclohex-2-en-1-one
3-(2,6-diethylheptyl)-cyclohex-2-en-1-one
3-(2,6-diethyloctyl)-cyclohex-2-en-1-one
3-(2-ethyl-6-methylheptyl)-cyclobut-2-en-1-one
3-(2-ethyl-6-methyloctyl)-cyclobut-2-en-1-one
3-(2,6,6-trimethylheptyl)-cyclopent-2-en-1-one
3-(2,6,6-trimethyloctyl)-cyclopent-2-en-1-one
3-(2,6-dimethyl-6-[methylthio]heptyl)-cyclopent-2-en-1-one
3-(2,6-dimethyl-5-heptenyl)-cyclopent-2-en-1-one
3-(5-(ethylthio)-2,4,5-trimethylhexyl)-cyclopent-2-en-1-one
3-(2,5-dimethyl-5-hexenyl)-cyclopent-2-en-1-one
3-(5-ethyl-2-methyl-5-(methylthio)heptyl)-cyclopent-2-en-1-one
3-(2,5-dimethyl-4-heptenyl)-cyclopent-2-en-1-one
3-(5-methyl-2-ethyl-5-(methylthio)heptyl)-cyclopent-2-en-1-one
3-(2-ethyl-6-methyl-5-heptenyl)-cyclopent-2-en-1-one
3-(2,4,5-triethyl-4-hexenyl)-cyclohex-2-en-1-one
3-(2,5-diethyl-5-(methylthio)hexyl)-cyclopent-2-en-1-one
3-(2-ethyl-6-methyl-5-octenyl)-cyclohex-2-en-1-one
3-(2-ethyl-6-methyl-6-(methylthio)heptyl)-cyclohex-2-en-1-one
3-(2,5,6-trimethyl-5-heptenyl)-cyclohex-2-en-1-one
3-(6-ethylthio-2,5,6-triethylheptyl)-cyclohex-2-en-1-one
3-(2,6-diethyl-5-octenyl)cyclobut-2-en-1-one

EXAMPLE 5

To 10 ml. of tetrahydrofuran at 0°, under nitrogen, is added 2.88 ml. of n-butyllithium (1.66M) and 0.389 g. of diisopropylamine. The reaction mixture is cooled to −80° and 0.334 g. of ethyl acetate is added. The reaction mixture is then stirred at −80° for 30 min. and 0.790 g. of (3-(2,6-dimethylheptyl)-cyclopent-2-en-1-one is added. After stirring at −80° for 40 minutes, 5 ml. of 10% aqueous hydrochloric acid is added dropwise and the mixture is warmed to room temperature. The solution is extracted with pentane and the pentane phase is then washed with brine, dried and concentrated to yield 0.900 g. of ethyl 7,11-dimethyl-3,5-ethylene-3-hydroxydodec-4-enoate.

Following the procedure of this Example using the ketones of Column IV as starting material, the esters of Column V are obtained.

V ethyl 7,10-diethyl-3,5-ethylene-3-hydroxy-undec-4-enoate
ethyl 3,5-ethylene-3-hydroxy-7,9,10-trimethylundec-4-enoate
ethyl 3,5-ethylene-3-hydroxy-7,10,10-trimethylundec-4-enoate
ethyl 2,5-dimethyl-3,5-ethylene-3-hydroxydodec-4-enoate
ethyl 3,5-ethylene-3-hydroxy-7,9,10-trimethyldodec-4-enoate
ethyl 3,5-ethylene-3-hydroxy-7,10,10-trimethyldodec-4-enoate
ethyl 3,5-ethylene-3-hydroxy-7-methylundec-4-enoate
ethyl 3,5-ethylene-3-hydroxy-7,10,10-triethylundec-4-enoate
ethyl 7,11-dimethyl-3,5-ethylene-3-hydroxytridec-4-enoate
ethyl 3-hydroxy-3,5-trimethylene-7,10,11-trimethyldodec-4-enoate
ethyl 3-hydroxy-3,5-trimethylene-7,10,11-trimethyltridec-4-enoate
ethyl 3-hydroxy-7-methyl-3,5-trimethylenedodec-4-enoate
ethyl 3-hydroxy-7-methyl-3,5-trimethylenetridec-4-enoate
ethyl 7,11-diethyl-3-hydroxy-3,5-trimethylenedodec-4-enoate
ethyl 7,11-diethyl-3-hydroxy-3,5-trimethylenetridec-4-enoate
ethyl 7-ethyl-3-hydroxy-11-methyl-3,5-methylenedodeca-4-enoate
ethyl 7-ethyl-3-hydroxy-11-methyl-3,5-methylenetrideca-4-enoate
ethyl 3,5-ethylene-3-hydroxy-7,11,11-trimethyldodeca-4-enoate
ethyl 3,5-ethylene-3-hydroxy-7,11,11-trimethyltrideca-4-enoate
ethyl 7,11-dimethyl-3,5-ethylene-3-hydroxy-11-(methylthio)dodec-4-enoate
ethyl 7,11-dimethyl-3,5-ethylene-3-hydroxydodeca-4,10-dienoate
ethyl 3,5-ethylene-10-ethylthio-3-hydroxy-7,9,10-trimethylundec-4-enoate
ethyl 7,10-dimethyl-3,5-ethylene-3-hydroxyundeca-4,9-dienoate
ethyl 10-ethyl-3,5-ethylene-3-hydroxy-7-methyl-10-(methyltion)dodec-4-enoate
ethyl 7,10-dimethyl-3,5-ethylene-3-hydroxydodeca-4,9-dienoate
ethyl 10-ethyl-3,5-ethylene-3-hydroxy-7-methyl-10-(methylthio-undec-4-enoate
ethyl 7-ethyl-3,5-ethylene-3-hydroxy-11-methyldodeca-4,10-dienoate
ethyl 3-hydroxy-7,9,10-triethyl-3,5-trimethyleneundeca-4,9-dienoate
ethyl 7,10-diethyl-3-hydroxy-10-methylthio-3,5-trimethyleneundec-4-enoate
ethyl 7-ethyl-3-hydroxy-11-methyl-3,5-trimethylenetrideca-4,10-dienoate
ethyl 7-ethyl-3-hydroxy-11-methyl-11-methylthio-3,5-trimethylenedodec-4-enoate
ethyl 3-hydroxy-7,10-11-trimethyl-3,5-trimethylenedodeca-4,10-dienoate
ethyl 11-ethylthio-3-hydroxy-7,10,11-triethyl-3,5-trimethylenedodec-4-enoate
ethyl 7,11-diethyl-3-hydroxy-3,5-methylenetrideca-4,10-dienoate By using acetic acid in place of ethyl acetate in the procedure of Example 5, there is obtained 7,11-dimethyl-3,5-ethylene-3-hydroxydodec-4-enoic acid.

Similarly, by repeating this process using each of the ketones of Column IV and acetic acid, the corresponding acid is obtained.

By using other esters, such as methyl acetate, isopropyl acetate, n-propyl acetate, prop-2-en-1-yl acetate, or prop-2-yn-1-yl acetate, in place of ethyl acetate in the process of Example 5, the respective esters are prepared, i.e., methyl 7,11-dimethyl-3,5-ethylene-3-hydroxydodec-4-enoate
isopropyl 7,11-dimethyl-3,5-ethylene-3-hydroxydodec-4-enoate
n-propyl 7,11-dimethyl-3,5-ethylene-3-hydroxydodec-4-enoate
prop-2'-en-1'-yl 7,11-dimethyl-3,5-ethylene-3-hydroxydodec-4-enoate
prop-2'-yn-1'-yl 7,11-dimethyl-3,5-ethylene-3-hydroxydodec-4-enoate

EXAMPLE 6

To a mixture of 3.04 mmols. of ethyl 7,11-dimethyl-3,5-ethylene-3-hydroxydodec-4-enoate and 3 ml. pyridine at 0° under nitrogen is added 0.8 ml. of phosphorus oxychloride. The reaction mixture is stirred at 0° for one-half hour and then is warmed to room temperature and is allowed to stand for 17 hours. The reaction mixture is then cooled to 0° and poured into a solution of ice and water. The organic portion is extracted with ether and the organic layer is separated and washed, in turn, with 10% aqueous hydrochloric acid, 5% aqueous sodium bicarbonate, and saturated aqueous sodium chloride and then is dried over sodium sulfate. The product is purified by preparative thin-layer chromatography (4:96 ethyl acetate/hexane) and distillation to yield 0.2 g. of ethyl 7,11-dimethyl-3,5-ethylenedodeca-2,4-dienoate, b.p. 138° at 0.06 mm.

Alternate means of dehydration by conventional methods, such as forming the corresponding 3-acetoxy compound and treating with potassium tert-butoxide are equally effective means of preparing the desired 2,4-diene compounds of this invention. Using the above methods of dehydration, the esters of Column VI corresponding to the hydroxy compounds of Column V are obtained.

VI ethyl 7,10-diethyl-3,5-ethyleneundeca-2,4-dienoate
ethyl 3,5-ethylene-7,9,10-trimethylundeca-2,4-dienoate
ethyl 3,5-ethylene-7,10,10-trimethylundeca-2,4-dienoate
ethyl 2,5-dimethyl-3,5-ethylenedodeca-2,4-dienoate
ethyl 3,5-ethylene-7,9,10-trimethyldodeca-2,4-dienoate
ethyl 3,5-ethylene-7,10,10-trimethyldodeca-2,4-dienoate
ethyl 3,5-ethylene-7-methylundeca-2,4-dienoate
ethyl 3,5-ethylene-7,10,10-trimethylundeca-2,4-dienoate
ethyl 7,11-trimethyl-3,5-ethylenetrideca-2,4-dienoate
ethyl 3,5-trimethylene-7,10,11-trimethyldodeca-2,4-dienoate
ethyl 3,5-trimethylene-7,10,11-trimethyltrideca-2,4-dienoate
ethyl 7-methyl-3,5-trimethylenedodeca-2,4-dienoate
ethyl 7-methyl-3,5-trimethylenetrideca-2,4-dienoate
ethyl 7,11-diethyl-3,5-trimethylenedodeca-2,4-dienoate
ethyl 7,11-diethyl-3,5-trimethylenetrideca-2,4-dienoate
ethyl 7-ethyl-11-methyl-3,5-methylenedodeca-2,4-dienoate
ethyl 7-ethyl-11-methyl-3,5-methylenetrideca-2,4-dienoate
ethyl 3,5-ethylene-7,11,11-trimethyldodeca-2,4-dienoate
ethyl 3,5-ethylene-7,11,11-trimethyltrideca-2,4-dienoate
ethyl 7,11-dimethyl-3,5-ethylene-11-(methylthio)-dodeca-2,4-dienoate
ethyl 7,11-dimethyl-3,5-ethylenedodeca-2,4,10-trienoate
ethyl 3,5-ethylene-10-ethylthio-7,9,10-trimethylundeca-2,4-dienoate
ethyl 7,10-dimethyl-3,5-ethyleneundeca-2,4,9-trienoate
ethyl 10-ethyl-3,5-ethylene-7-methyl-10-(methylthio)dodeca-2,4-dienoate
ethyl 7,10-dimethyl-3,5-ethylenedodeca-2,4,9-trienoate
ethyl 10-ethyl-3,5-ethylene-7-methyl-10-(methylthio)undeca-2,4-dienoate
ethyl 7-ethyl-3,5-ethylene-11-methyldodeca-2,4,10-trienoate
ethyl 7,9,10-triethyl-3,5-trimethyleneundeca-2,4,9-trienoate
ethyl 7,10-diethyl-10-methylthio-3,5-trimethyleneundeca-2,4-dienoate
ethyl 7-ethyl-11-methyl-3,5-trimethylenetrideca-2,4,10-trienoate
ethyl 7-ethyl-11-methyl-11-methylthio-3,5-trimethylenedodeca-2,4-dienoate
ethyl 7,10,11-trimethyl-3,5-trimethylenedodeca-2,4,10-trienoate
ethyl 11-ethylthio-7,11-triethyl-3,5-trimethylenedodeca-2,4-dienoate
ethyl 7,11-diethyl-3,5-methylenetrideca-2,4,10-trienoate

EXAMPLE 7

A mixture of 1 g. of ethyl 7,11-dimethyl-3,5-ethylenedodeca-2,4-dienoate, 60 ml. of methanol, 0.5 g. of potassium hydroxide and 6 ml. of water is heated to reflux for about eight hours. The mixture is then diluted with water, neutralized and extracted with ether. The organic phase is washed with water, dried over sodium sulfate, and evaporated to yield 7,11-dimethyl-3,5-ethylenedodeca-2,4-dienoic acid.

Using the foregoing procedure, the other esters of Column VI are hydrolyzed to produce the respective free acids.

EXAMPLE 8

To a solution of six equivalents of acetyl chloride in six equivalents of methanol at 0° is added one equivalent of ethyl 7,11-dimethyl-3,5-ethylenedodeca-2,4,10-trienoate and the resulting mixture is allowed to stand for about two days at 0°. The mixture is evaporated under reduced pressure to yield ethyl 11-chloro-7,11-dimethyl-3,5-ethylenedodeca-2,4-dienoate which is purified by preparative thin-layer chromatography.

The above process is repeated using each of the triene esters of Column VI to prepare the respective compound of Column VII.

VII ethyl 10-chloro-7,10-dimethyl-3,5-ethyleneundeca-2,4-dienoate
ethyl 10-chloro-7,10-dimethyl-3,5-ethylenedodeca-2,4-dienoate
ethyl 11-chloro-7-ethyl-3,5-ethylene-11-methyldodeca-2,4-dienoate
ethyl 11-chloro-7,9,10-triethyl-3,5-trimethyleneundeca-2,4-dienoate
ethyl 11-chloro-7-ethyl-11-methyl-3,5-trimethylenetrideca-2,4-dienoate
ethyl 11-chloro-7,10,11-trimethyl-3,5-trimethylenedodeca-2,4-dienoate
ethyl 11-chloro-7,11-diethyl-3,5-methylenetrideca-2,4-dienoate

EXAMPLE 9

To a mixture of 1.9 g. of mercuric acetate, 6 ml. of water and 20 ml. of tetrahydrofuran is added 1.49 g. of ethyl 7,11-dimethyl-3,5-ethylenedodeca-2,4,10-trienoate. After addition, the reaction mixture is stirred for about 20 minutes. The mixture is cooled to about 0° and 6 ml. of aqueous sodium hydroxide (3molar) is added followed by 0.49 g. of sodium borohydride is aqueous sodium hydroxide (about 3molar). The mixture is stirred for about 30 minutes. The mixture is then decanted, concentrated, diluted with water and then extracted with ether. The ethereal extract is washed with water, dried over magnesium sulfate and the product chromatographed on silica to give ethyl 11-hydroxy-7,11-dimethyl-3,5-ethylenedodeca-2,4-dienoate.

The above process is repeated using each of the triene esters of Column VI to prepare the respective compounds of Column VIII.

VIII ethyl 10-hydroxy-7,10-dimethyl-3,5-ethyleneundeca-2,4-dienoate
ethyl 10-hydroxy-7,10-dimethyl-3,5-ethylenedodeca-2,4-dienoate
ethyl 11-hydroxy-7-ethyl-3,5-ethylene-11-methyldodeca-2,4-dienoate
ethyl 10-hydroxy-7,9,10-triethyl-3,5-trimethyleneundeca-2,4-dienoate ethyl 11-hydroxy-7-ethyl-11-methyl-3,5-trimethylenetrideca-2,4-dienoate
ethyl 11-hydroxy-7,10,11-trimethyl-3,5-trimethylenedodeca-2,4-dienoate
ethyl 11-hydroxy-7,11-diethyl-3,5-methylenetrideca-2,4-dienoate

EXAMPLE 10

To a solution of 2 g. of ethyl 7,11-trimethyl-3,5-ethylenedodeca-2,4,10-trienoate in 20 ml. of ethanol, cooled to 0° in an ice bath, is added a suspension of 2.32 g. of mercuric acetate in 50 ml. of ethanol over 15 minutes. The reaction mixture is stirred for two hours and then, with cooling, 1.22 g. of potassium hydroxide in 20 ml. of ethanol is added. Then 0.139 g. of sodium borohydride is added in small portions and stirring continued for 30 minutes. The solution is decanted, then concentrated to half volume, diluted with 100 ml. of water and extracted with ether (3 × 50). The ethereal phase is washed with water, dried over magnesium sulfate and the crude product chromatographed on silica using hexane:ether to yield ethyl 11-ethoxy-3,5-ethylene-7,11-dimethyldodeca-2,4-dienoate.

The above process is repeated using each of the triene esters of Column VI to prepare the respective compounds of Column IX.

IX ethyl 10-ethoxy-7,10-dimethyl-3,5-ethyleneundeca-2,4-dienoate
ethyl 10-ethoxy-7,10-dimethyl-3,5-ethylenedodeca-2,4-dienoate
ethyl 11-ethoxy-7-ethyl-3,5-ethylene-11-methyldodeca-2,4-dienoate
ethyl 10-ethoxy-7,9,10-triethyl-3,5-trimethyleneundeca-2,4-dienoate
ethyl 11-ethoxy-7-ethyl-11-methyl-3,5-trimethylenetrideca-2,4-dienoate
ethyl 11-ethoxy-7,10,11-trimethyl-3,5-trimethylenedodeca-2,4-dienoate
ethyl 11-ethoxy-7,11-diethyl-3,5-methylenetrideca-2,4-dienoate Similarly, by using methanol in place of ethanol in the process of Example 10, the corresponding methoxy compounds, e.g. ethyl 11-methoxy-3,5-ethylene-7,11-dimethyldodeca-2,4-dienoate, are prepared.

EXAMPLE 11

To 0.55 g. of 11-methoxy-7,11-dimethyl-3,5-ethylenedodeca-2,4-dienoic acid in 10 ml. of dry benzene is added 0.21 ml. of oxalyl chloride. The mixture is stirred occasionally at room temperature for about 2.5 hours. The mixture is cooled in cold water and then 0.18 ml. of ethylmercaptan is added with stirring, following by dropwise addition of 0.16 ml. of pyridine. The mixture is then stirred at room temperature for about one hour. Ether and saturated sodium bicarbonate is added and the organic phase separated. The organic phase is washed with water, aqueous sodium bicarbonate, saturated sodium chloride, dried over calcium sulfate and evaporated to yield S-ethyl 3,5-ethylene-11-methoxy-7,11-dimethyldodeca-2,4-dienethioate.

Thiol esters are prepared using each of methyl mercaptan, n-propyl mercaptan, isopropyl mercaptan, isobutyl mercaptan, n-butyl mercaptan, prop-2-en-1-yl mercaptan and prop-2-yn-1-yl mercaptan in reaction with 3,5-ethylene-11-methoxy-7,11-dimethyldodeca-2,4dienoyl chloride or the sodium salt of 3,5-ethylene-11-methoxy-7,11-dimethyldodeca-2,4-dienoic acid to yeild:

S-methyl 3,5-ethylene-11-methoxy-7,11-dimethyldodeca-2,4-dienethioate
S-n-propyl 3,5-ethylene-11-methoxy-7,11-dimethyldodeca-2,4-dienethioate
S-isopropyl 3,5-ethylene-11-methoxy-7,11-dimethyldodeca-2,4-dienethioate
S-isobutyl 3,5-ethylene-11-methoxy-7,11-dimethyldodeca-2,4-dienethioate
S-n-butyl 3,5-ethylene-11-methoxy-7,11-dimethyldodeca-2,4-dienethioate
S-prop-2'-en1'-yl 3,5-ethylene-11-methoxy-7,11-dimethyldodeca-2,4-dienethioate
S-prop-2'-yn-1'-yl 3,5 ethylene-11-methoxy-7,11-dimethyldodeca-2,4-dienethioate

EXAMPLE 12

Three grams of 7,11-dimethyl-3,5-ethylenedodeca-2,4-dienoyl chloride in benzene is mixed with 2.5 g. of diethylamine in benzene and the resulting mixture allowed to stand at room temperature for about two hours. The mixture is concentrated under reduced pressure and the residue taken up in benzene, washed with dilute aqueous sodium bicarbonate and water, dried over sodium sulfate and evaporated to yield N,N-diethyl 7,11-dimethyl-3,5-ethylenedodeca-2,4-dienamide.

By use of the foregoing procedure, each of dimethylamine, ethylamine, allylamine and propenylamine is reacted with the acid chloride to yield the corresponding amide, that is, N,N-dimethyl 7,11-dimethyl-3,5-ethylenedodeca-2,4-dienamide, N-ethyl 7,11-trimethyl-3,5-ethylenedodeca-2,4-dienamide, etc.

EXAMPLE 13

To a stirred solution of 2.4 g. of 7,11-dimethyl-3,5-ethylenedodeca-2,4-dienoic acid in 20 ml. of dry ether is added slowly at 0°, 23 ml. of a one molar solution of ethyl lithium in benzene. After about three hours at 20°, the mixture is poured into iced 1N hydrochloric acid (100 ml.) with vigorous stirring. The ether layer is separated, combined with ethereal washings of the aqueous phase, washed with water, saturated potassium bicarbonate and then saturated brine, dried over magnesium sulfate and concentrated under reduced pressure to yield 9,13-dimethyl-5,7-ethylenetetradeca-4,6-dien-3-one, which can be purified by chromatography.

By using methyl lithium, n-propyl lithium and n-butyl lithium in the above process in place of ethyl lithium, there is prepared 8,12-trimethyl-4,6-ethylenetrideca3,5-dien-2-one, 10,14-dimethyl-6,8-ethylenepentadeca-5,7-dien-4-one and 11,15-dimethyl-7,9-ethylene hexadeca-6,8-dien-5-one, respectively.

*Galleria mellonella* pupae, less than 24 hours old, maintained as larvae at 31° C. room temperature, humidity of about 70% and photo-period of 16 hours, were treated topically at appropriate dosage rates of 0.001, 0.01, and 0.1 micrograms of ethyl 7,11-dimethyl-3,5-ethylenedodeca-2,4-dienoate tested using acetone as the carrier. Ten specimens were treated per dose level and one acetone control was prepared for each assay. Two replicates were made of the test at each dosage rate. The compound was applied topically on that ventral portion of the pupa where the wings meet over the abdomen, using a sryinge. Scoring was done when all adults had emerged in the controls, usually ten days after treatment by determining the degree of morphogenetic aberrations (inhibition of adult development) in all specimens. The $ID_{50}$, determined by interpolation after plotting on semi-logarithmic paper the dose on the horizontal axis and the percent response on the vertical axis, for inhibition of development of a group of pupae to adults is less than 0.01 µg. per pupae.

EXAMPLE 14

A. A mixture of 11.2 g. of dihydroresocinol, 20 ml. of 2-methyl-1-propanol, 100 ml. of benzene and about 100 mg. of p-toluenesulfonic acid is heated at reflux overnight with water removed via Dean Stark trap. After cooling, mixture treated with solid sodium carbonate and poured into 10% sodium hydroxide, washed with 10% sodium hydroxide and water dried and evaporated to yield the enone

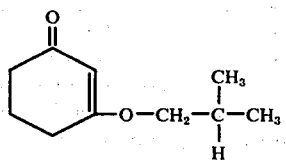

B. A solution of 11 g. of 1-chloro-2,6-dimethylheptane in 70 ml. ether is cooled to 0° and treated with 150 mm. of lithium wire under argon (1.05 g.) at −10° to 0° for four hours to yield a 0.9M solution.

C. A solution of 3.9 g. of the enone of Part A in ether at −78° is treated with 25 ml. of the lithium reagent of part B and the reaction mixture allowed to reach room temperature. The mixture is poured into ice cold 5% sulfuric acid and stirred for 10 minutes at 0°. The ether layer is separated and aqueous phase extracted with ether. Ether phase is washed with 10% sodium hydroxide and water, dried and evaporated and residue short-path distilled to yield 3-(2,6-dimethylheptyl)-cyclopent-2-en-1-one, b.p. (bath) 90°-100° (0.05 mm.).

D. A solution of 2.82 ml. of diisopropylamine in 40 ml. of dry tetrahydrofuran is treated with 12.5 of 1.6 M n-butyllithium at −78°. To this solution is added 3.65 g. of ethyl trimethylsilylacetate slowly. After about 10 minutes. a solution of the enone of part C (2.02 g.) in 10 ml. of tetrahydrofuran is added. After one hour at −78° and 3 hours at −25°, reaction is poured into water and extracted with hexane. The combined hexane extract is water with 1N sulfuric acid, sodium bicarbonate and water, dried and evaporated to an oily residue. The residue is applied to 1 m. silica plates and eluted with 3% ethyl acetate/hexane. The lower major UV active bands are removed and washed off with 4% ethanol/chloroform. After removal of solvent, residue distilled yielding ethyl 7,11-dimethyl-3,5-ethylenedodeca-2,4-dienoate, b.p. (bath) 130°-135° (0.05 mm.), mostly trans isomer.

EXAMPLE 15

Part B and C of Example 14 are repeated using 1-chloro-2,6-dimethyl-5-methoxyheptane to yield 3-(5-methoxy-2,6-dimethylheptyl)-cyclopent-2-en-1-one which is used as the starting material in part D of Example 14 to yield ethyl 10-methoxy-7,11-dimethyl-3,5-ethylenedodeca-2,4-dienoate.

EXAMPLE 16

To a solution of 28 g. of freshly distilled melonal in 300 ml. of absolute methanol is added 20 ml. of trimethyl orthoformate and one g. of chloroacetic acid. The reaction mixture is allowed to stand at room temperature for 48 hours and then 5 g. of solid sodium bicarbonate is added. After stirring for one hour, the mixture if filtered and the solvent evaporated to give melanol dimethylacetal (1,1-dimethoxy-2,6-dimethyl-5-heptene).

Alternatively, the dimethyl acetal can be prepared by the procedure described in U.S. Pat. No. 3,826,804 using ammonium chloride, methanol and trimethylorthoformate at room temperature.

A solution of 55.8 g. of melonal dimethyl acetal in 200 ml. of dry tetrahydrofuran is cooled to 0° and then 200 ml. of 1M borane in tetrahydrofuran is added dropwise at 0°. The reaction mixture is stored overnight at 0° and then about 300 ml. of 2N sodium hydroxide is added followed by cautious addition of 50 ml. of 30% hydrogen peroxide while stirring. The mixture is then extracted with ether and solvent removed under reduced pressure to give crude 1,1-dimethoxy-5-hydroxy-2,6-dimethylheptane which can be purified by distillation.

To a mixture of 2.4 g. of clean sodium hydride in 200 ml. of dry tetrahydrofuran containing 20 ml. of dry HMPT (hexamethylphosphorictriamide) is added dropwise a solution of 20.4 g. of 1,1-dimethoxy-5-hydroxy-2,6-dimethylheptane in dry tetrahydrofuran. The mixture is stirred at room temperature until evolution of hydrogen ceases and then 16 g. of methyl iodide is added. The reaction mixture is refluxed for 3 hours and then cooled, diluted with water and extracted with ether. The etheral extracts are evaporated under reduced pressure to yield crude 1,1,5-trimethoxy-2,6-dimethylheptane which can be purified by distillation or chromatography on Florisil.

A solution of 10.9 g. of 1,1,5-trimethoxy-2,6-dimethylheptane in 200 ml. of tetrahydrofuran and 60 ml. of water is treated with one g. of trichloroacetic acid and then the mixture heated at 60° for one hour. After cooling, there is added 40 ml. of 2N sodium hydroxide in methanol followed by 2 g. of powdered sodium borohydride. The reaction mixture is stirred at room temperature for three hours and then concentrated and extracted with ether. The ethereal extracts are evaporated under reduced pressure to give crude 1-hydroxy-5-methoxy-2,6-dimethylheptane which can be purified by distillation.

A mixture of 3.4 g. of 1-hydroxy-5-methoxy-2,6-dimethylheptane and 3 g. of thionyl chloride and 60 ml. of dry benzene is treated with 0.2 ml. of dry dimethylformamide and then refluxed for 6 hours. After cooling, the mixture is decanted and 1-chloro-5-methoxy-2,6-dimethylheptane isolated by filtration through silica gel and distillation.

The C-1 chloride (or bromide) can be prepared also by first converting the alcohol to the mesylate or tosylate which is then reacted with lithium chloride (or lithium bromide) in acetone (cf. Willy and Henrick, U.S. Pat. No. 3,801,612).

What is claimed is:
1. A compound of the formula:

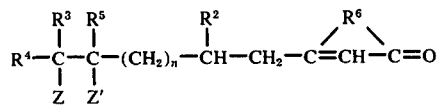

wherein,
each of $R^2$ and $R^4$ is lower alkyl;
each of $R^3$ and $R^5$ is hydrogen or lower alkyl;
$R^6$ is methylene, ethylene or trimethylene;
$n$ is one, two or three;
Z is hydrogen, chlorine, lower alkyl or one of the groups —OR or —SR in which R is hydrogen or lower alkyl; and
Z' is hydrogen or together with Z forms a carboncarbon bond.

2. A compound according to claim 1 wherein $n$ is one or two; $R^2$ is methyl or ethyl; $R^5$ is hydrogen or methyl; $R^3$ is hydrogen, methyl or ethyl; $R^4$ is lower alkyl of one to three carbon atoms; Z is hydrogen, methyl, hydroxy, methoxy or ethoxy; and Z' is hydrogen or together with Z forms a carbon carbon bond.

3. A compound according to claim 2 of the formula

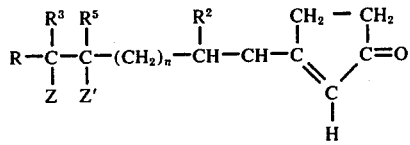

4. A compound according to claim 3 wherein $R^3$ is methyl or ethyl; $n$ is two; Z' is hydrogen or together with Z is a carbon-carbon bond, and Z is hydrogen, methoxy ro ethoxy.

5. A compound according to claim 4 wherein each of $R^2$, $R^3$ and $R^4$ is methyl, $R^5$ is hydrogen and z is hydrogen.

6. A compound according to claim 4 wherein each of $R^2$, $R^3$ and $R^4$ is methyl, $R^5$ is hydrogen and Z' together with Z is a carbon-carbon bond.

7. A compound according to claim 3 wherein $n$ is one; $R^2$ is methyl; each of $R^3$, $R^5$ and Z' is hydrogen, $R^4$ is isopropyl; and Z is methoxy.

8. A compound according to claim 3 wherein each of $R^2$, $R^3$ and $R^4$ is methyl; each of $R^5$ and Z' is hydrogen; $n$ is two; and Z is methoxy or ethoxy.

* * * * *